United States Patent [19]

Garcia

[11] Patent Number: 4,875,476

[45] Date of Patent: Oct. 24, 1989

[54] ANKLE SUPPORT BANDAGE FOR PREVENTION OF ANKLE INJURY

[75] Inventor: Mario C. Garcia, West St. Paul, Minn.

[73] Assignee: Prevent Products, Inc., St. Louis Park, Minn.

[21] Appl. No.: 158,559

[22] Filed: Feb. 22, 1988

Related U.S. Application Data

[63] Continuation-in-part of Ser. No. 936,454, Dec. 1, 1986, abandoned.

[51] Int. Cl.⁴ .............................................. A61F 13/00
[52] U.S. Cl. .................................... 128/157; 128/156; 128/166
[58] Field of Search ................. 128/94, 134, 158, 166, 128/80 R, 80 H, 82, 89 R, 90, 94, 87, 156, 166, 166.5, 169; 604/304

[56] References Cited

U.S. PATENT DOCUMENTS

| | | |
|---|---|---|
| 991,831 | 5/1911 | Collis . |
| 1,211,055 | 1/1917 | Bernstein . |
| 1,441,907 | 1/1923 | Bernstein . |
| 1,478,253 | 12/1923 | Quenzer . |
| 1,741,826 | 12/1928 | Christy . |
| 2,013,757 | 5/1930 | Jung, Jr. . |
| 3,050,053 | 8/1962 | Peckham . |
| 3,383,708 | 5/1968 | Pappas ............................ 128/166 |
| 3,584,622 | 6/1971 | Domenico . |
| 3,777,751 | 12/1973 | Wise . |
| 3,805,781 | 4/1974 | Hoey . |
| 4,345,590 | 9/1982 | Nakajima . |
| 4,369,775 | 1/1983 | Gamm . |

Primary Examiner—Richard J. Apley
Assistant Examiner—N. Paul
Attorney, Agent, or Firm—Orrin M. Haugen; Thomas J. Nikolai; Frederick W. Niebuhr

[57] ABSTRACT

A support bandage for providing temporary support and at least partial immobilization of the ankle joint which comprises an "L"-shaped bandage, the entire underside of which is coated with adhesive of the type typically used for adhesive bandages. One segment of the "L" bandage is applied over the ankle joint and continuously across the underside of the arch of the foot, and up to the opposite side of the ankle joint. The other segment of the "L"-shaped support bandage is thereafter wrapped about the periphery of the ankle joint, securing the free end of the first-to-be-applied segment. The arrangement employs wide elongated strips of adhesive-backed tape which are fixedly arranged in a generally right angular relationship, one to the other in order to form the "L"-shaped arrangement. The utilization of a single wide strip provides for a more secure and uniform application of immobilizing force to the ankle area.

4 Claims, 2 Drawing Sheets

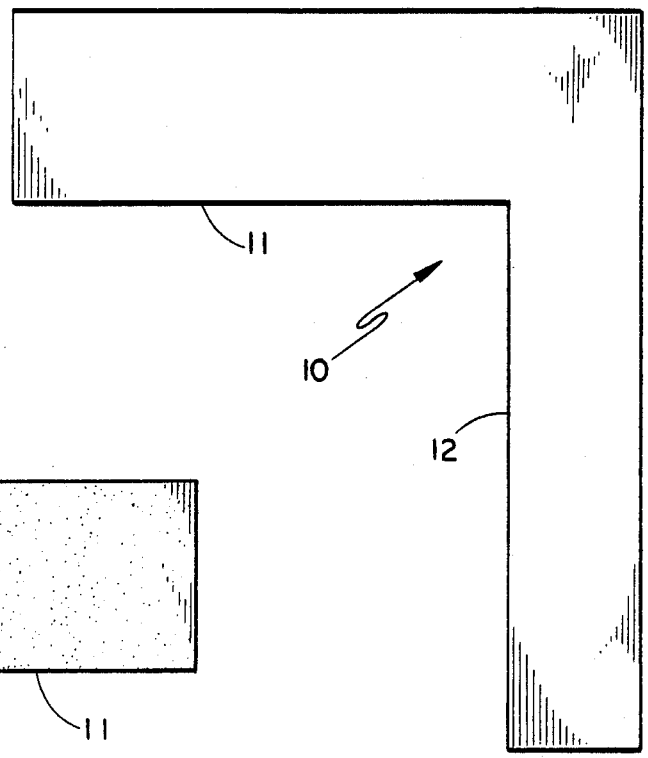
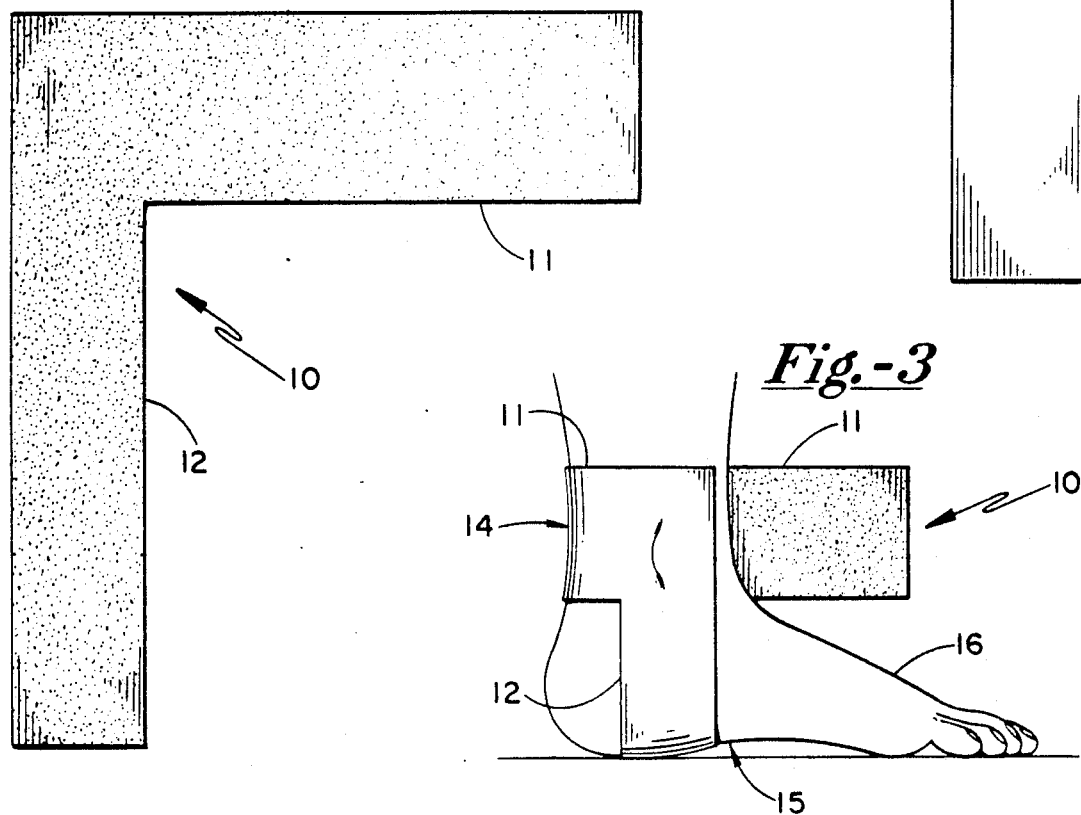
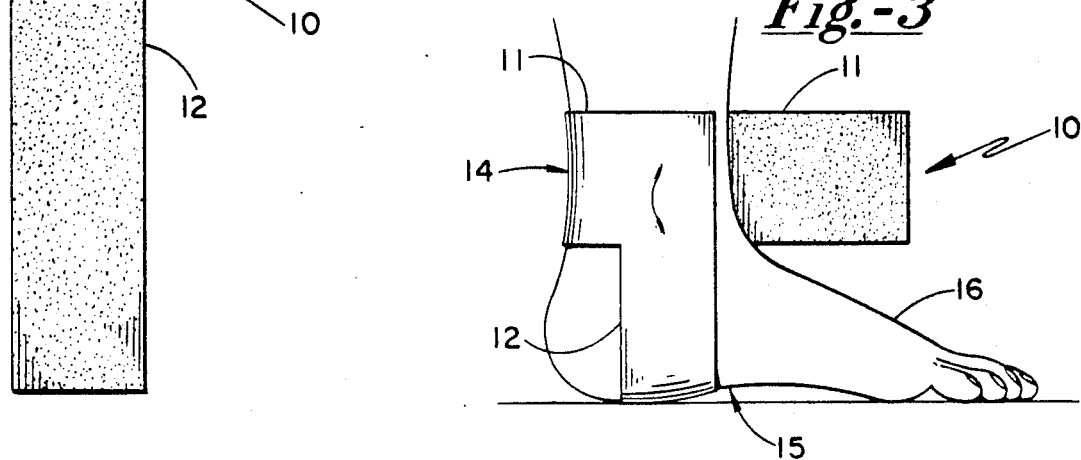
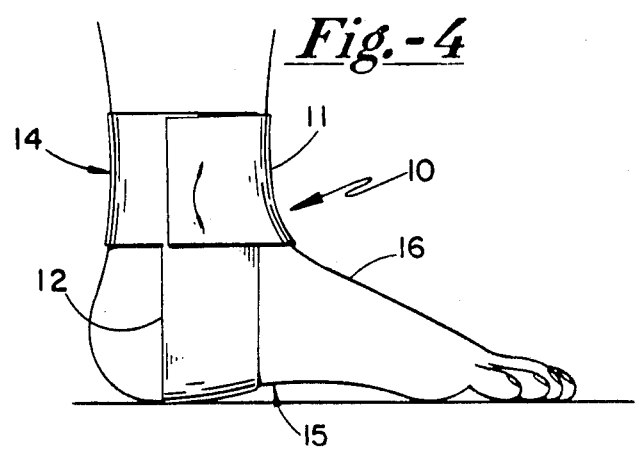

ANKLE SUPPORT BANDAGE FOR PREVENTION OF ANKLE INJURY

CROSS-REFERENCE TO RELATED APPLICATION

The present application is a Continuation-in-Part of my application Ser. No. 06/936,454, filed Dec. 1, 1986, entitled "ANKLE SUPPORT BANDAGE FOR PREVENTION OF ANKLE INJURY" now abandoned.

BACKGROUND OF THE INVENTION

The present invention relates generally to an adhesive bandage arrangement to provide for temporary and supplementary support for the ankle for preventing injury or trauma to the area such as a sprain or the like. The present invention includes an adhesive plaster support formed in a fashion such that improved and enhanced support is obtainable due to the design and configuration of the bandage.

Frequently, individuals experience sprains and/or other damage to the ankle area, and temporary support for at least partial immobilization of the ankle joint frequently aids in the prevention of such injury or, if an injury has already occurred, to aid in the healing process. Individuals suffer sprains from a variety of causes, and these individuals come from a total cross-section of the population. Healthy, active individuals as well as mostly inactive sedentary individuals suffer from ankle sprains from time to time.

Most frequently, however, athletes or individuals engaged in athletics suffer sprains. In order to assist these individuals in remaining active and mobile, ankle supports in the form of adhesive plasters and adhesive-backed tape have been employed, as well as conventional ankle wrapping with elastic bandages.

While ankle wrapping procedures, particularly conventional ankle wrapping procedures utilizing adhesive-backed tape (adhesive tape) are common and straightforward, these procedures frequently involve the use of relatively thin individual strips such as in the area of about one-inch in width of adhesive tape applied on a sequential basis to form the ankle support bandage. Frequently, when undertaking such a wrapping procedure, different angular dispositions as well as different degrees of tension are set up in the individual strips. As a result, the support achieved by such an adhesive means lacks uniformity from one edge to the other.

Conventional ankle wrapping procedures normally include the utilization of one group of elongated strips which extend from the lateral portions of the ankle and under the arch of the foot in a generally "U"-shaped configuration. Following the placing of these strips or segments upon the ankle-arch area, there is thereafter placed a series of adhesive bands or strips about the ankle joint. Typically, the ankle joint is defined as that zone lying adjacent the distal end of the fibula and tibia, or talus. The wrapping of the ankle with a peripheral wrap normally covers the free ends of the "U"-shaped members previously set in place so as to complete the formation of the ankle support. Again, this procedure frequently results in the formation of a support in which the tension varies from one edge to the other, as well as from one side to the other.

SUMMARY OF THE INVENTION

Briefly, in accordance with the present invention, an ankle support bandage is provided for sprains and similar injuries to the ankle which comprises an adhesive-backed tape means of a generally "L"-shaped support bandage. The bandage comprises, in a unitary configuration, two wide elongated strips or legs of adhesive-backed tape fixedly arranged in right angular relationship, one to the other. The entire undersurface of the support bandage is coated with adhesive of the type typically used for adhesive bandages. The support bandage provides means for adhesively securing a first of the wide strips beneath the arch of the foot of the patient, and with each end, including the free end thereof extending to and covering virtually all of the exterior of the ankle joint area, such as the talus area. Thereafter, the remaining elongated strip of the "L"-shaped bandage is adhesively secured around the periphery of the ankle about the ankle joint, and also covering the free end of the first-to-be-applied elongated strip so as to secure the entire support bandage about the ankle zone as well as under the instep.

Therefore, it is a primary object of the present invention to provide an improved ankle support bandage for sprains which utilizes an adhesive-backed tape in the form of a generally "L"-shaped support bandage with two wide elongated strips of adhesive-backed tape fixedly arranged together in generally right angular relationship, one to the other, and with the support bandage being arranged so that one strip may be secured in a generally "U" form from the ankle joint underneath the arch, and with the other strip being wrapped around the periphery of the ankle securing the free end of the other strip in place.

It is yet a further object of the present invention to provide an improved ankle support bandage and means for applying the bandage to prevent injury to an ankle and for temporary support thereof, and wherein the ankle support bandage comprises a generally "L"-shaped support bandage of two wide generally elongated strips of adhesive-backed tape fixedly arranged in a generally right angular relationship, one to the other, with one strip being adapted to extend from the ankle joint beneath the arch, and with the other strip being applied around the periphery of the ankle.

Other and further objects of the present invention will become apparent to those skilled in the art upon a study of the following specification, appended claims, and accompanying drawing.

IN THE DRAWINGS

FIG. 1 is a top plan view of the ankle support bandage prepared in accordance with the present invention;

FIG. 2 is a bottom plan view of the support bandage illustrated in FIG. 1, and showing the adhesive coating over the entire bottom surface;

FIG. 3 is a side elevational view of a portion of a patient's leg showing the ankle and foot together with the adhesive support bandage of the present invention being applied thereto;

FIG. 4 is a view similar to FIG. 3, showing the other side of the ankle, and showing the adhesive support bandage of the present invention secured in place;

DESCRIPTION OF THE PREFERRED EMBODIMENT

Figure 5:
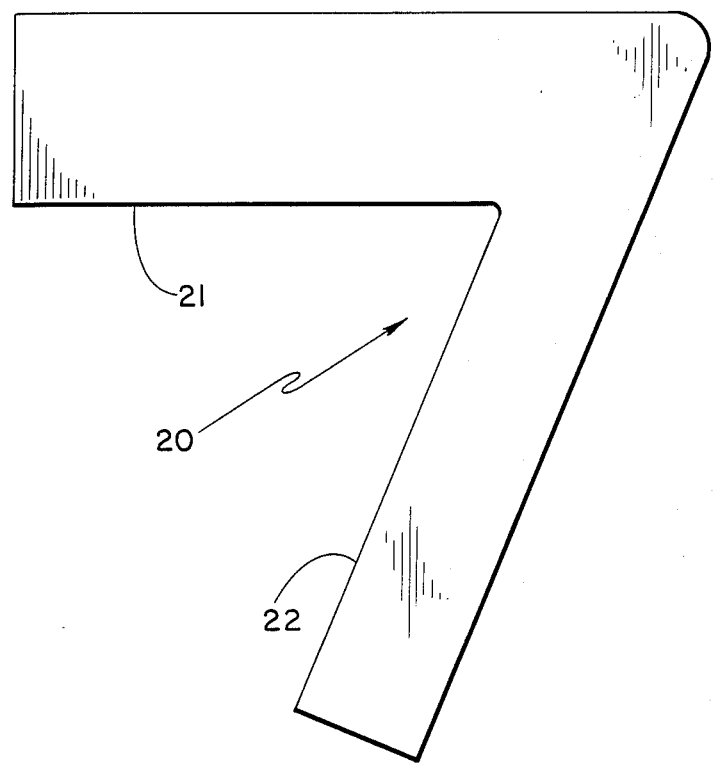
FIG. 5 is a view similar to FIG. 1 showing a modified embodiment of the present invention.

In accordance with the preferred embodiment of the present invention, the ankle support bandage of the present invention comprises an adhesive-backed tape means generally designated 10, which is in a generally "L"-shaped configuration. Two wide generally elongated strips 11 and 12 are fixedly arranged generally at right angular relationship, one to another, with the upright portion of the "L" being illustrated at 12, and with the base of the "L" being shown at 11. The support bandage provides means for adhesively securing the bandage 10 to the ankle zone of a patient so as to cover the ankle joint area. Typically, this is an adhesive such as is commonly used in adhesive tape and/or adhesive plasters arranged to cover the entire underside of the bandage. Such tapes are, of course, commercially available. In the present arrangement, however, the "L"-shaped support bandage 10 is arranged so that the two legs of the "L" are fixedly secured, one to another, prior to the time that the support bandage is applied to the ankle of the patient.

As is indicated in the drawing, one of the two wide generally elongated strips, such as strip 12 is secured to the patient from the ankle zone beneath the arch of the foot. Each end portion including the free end portion of the adhesive extends upwardly so that it adequately covers the ankle joint defined as that zone lying at the distal ends of the fibula and tibia. This application of the ankle support bandage is illustrated in FIG. 3. In particular, one of the two wide generally elongated strips such as strip 12 is shown as extending from the ankle area around the underside of the arch of the foot. Upon completion of the application of the first wide elongated strip, the second strip such as strip 11 is wrapped about the ankle so as to capture the free end of the first-to-be-applied strip 12 thereunder.

Briefly, and in accordance with the drawing of FIGS. 3 and 4, the ankle support bandage 10 is shown as being wrapped about the ankle area generally designated 14, and with the strip extending beneath the arch area generally designated 15 of foot 16.

While the strips have been defined as "wide generally elongated" in their configurations, a typical dimension for an individual normal size would be as follows:

| | |
|---|---|
| Strip 11 | approx. 4" × 12" |
| Strip 12 | approx. 2¾" × 15" |

For individuals of smaller stature, a somewhat smaller configuration may be utilized, while those larger individuals may require an ankle support bandage of somewhat larger dimension. Generally, however, the arrangements should be similar in configuration, so that an adequate, but not excessive, amount of the arch area is covered by strip 12, and an adequate amount of the flexural portions of the ankle is covered by the wide generally elongated strip 11.

As indicated above, the ankle support bandage of the present invention makes it possible for an ankle to be supported by applying a support bandage thereto which, when applied, is provided with uniform tension across the width of the support tape, and with uniform support forces thereby being applied.

Turning now to FIG. 5 of the drawings, the modified embodiment illustrates two features different from those illustrated in the embodiment FIGS. 1–4 inclusive. Specifically, the bandaging device 20 includes a pair of angularly disposed legs 21 and 22, which are joined at an apex zone defined by a radius or arcuate segment. It has been found that the utilization of the arcuate configuration at the apex reduces the tendency toward ripping, and may, of course, be applied to the embodiment of FIGS. 1–4 as well. The outer apex zone is also noted, with the radius of arc being generally equal between the inner and outer apices.

Figure 6:
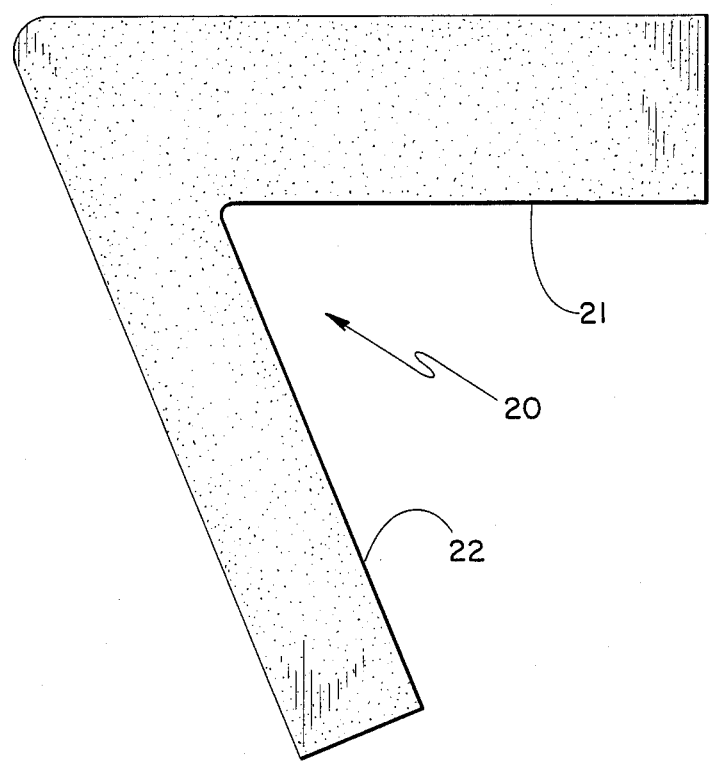
FIG. 6 is a view similar to FIG. 2 illustrating the modified embodiment of FIG. 5 of the side to which the adhesive is applied.

In its utilization, the embodiment of FIGS. 5 and 6, with the legs 21 and 22 joining at an acute angle, provide a means for applying the device which may include some advantages in utilization. In the embodiment of FIGS. 5 and 6, it is possible to utilize the device in the same fashion as the device of FIGS. 1–4, but including support at a zone in the arch which is somewhat different from that of the right-angled device of FIGS. 1–4. Some flexibility in application is accordingly possible.

Furthermore, the device of FIGS. 5 and 6 may find application in support of joints other than ankle joints, including knee joints. In support the knee joints, two devices of the type shown in FIGS. 5 and 6 may be utilized in criss-cross form, thereby supporting the knee joint in a fashion reducing the tendency toward lateral flexure.

What is claimed is:

1. Adhesive-backed tape means for providing temporary support to the ankle of a human and comprising:
   (a) a generally "L"-shaped support bandage of two wide generally elongated strips of adhesive-backed tape fixedly arranged in generally right angular relationship, one to the other and with said adhesive backing being substantially uniform and extending across the entire extent of said two elongated strips;
   (b) means for adhesively securing a first of said wide strips beneath the arch of the foot of the patient, and with each end, including the free end thereof, extending to and covering a portion of the ankle; and
   (c) means for adhesively securing the other of said wide elongated strips about the ankle so as to overlie said free end and adhesively bond said free end onto the ankle of the patient.

2. The method of providing temporary support to the human ankle and comprising the steps of:
   (a) placing a first leg of a generally "L"-shaped support bandage of two wide generally elongated strips with back surfaces thereof being completely and substantially uniformly covered with an adhesive-backed coating, said tape strips being fixedly arranged in generally right angular relationship, one to the other, in a generally "U"-shaped configuration beneath the arch of a patient's foot and adhesively securing said elongated strip thereto; and
   (b) placing the other leg of said ankle support bandage about the periphery of the ankle of the patient at the zone surrounding the distal end of the fibula and tibia and adhesively securing said elongated strip to the ankle and overlying the free end of said first leg.

3. The adehsive-backed tape means as defined in claim 1 wherein the elongated strips are joined through an arcuate segment at inner and outer apices.

4. Adhesive-backed tape means for providing temporary support to the ankle of a human and comprising:
 (a) a generally "L"-shaped support bandage of two wide generally elongated strips of adhesive-backed tape fixedly arranged in acute angular relationship, one to the other and with said adhesive backing being substantially uniform and extending across the entire extent of the back surface of said two elongated strips;
 (b) means for adhesively securing a first of said wide strips beneath the arch of the foot of the patient, and with each end, including the free end thereof, extending to and covering a portion of the ankle; and
 (c) means for adhesively securing the other of said wide elongated strips about the ankle so as to overlie said free end and adhesively bond said free end onto the ankle of the patient.

* * * * *